United States Patent
Chung et al.

(10) Patent No.: US 7,409,239 B2
(45) Date of Patent: Aug. 5, 2008

(54) METHOD FOR PREDICTING THE BLOOD GLUCOSE LEVEL OF A PERSON

(75) Inventors: Joanne Wai Yee Chung, Hong Kong (HK); Ka Lun Fan, Hong Kong (HK); Thomas Kwok Shing Wong, Hong Kong (HK); Simon Chak Hing Lam, Hong Kong (HK); Ching Ching Cheung, Hong Kong (HK); Chung Man Chan, Hong Kong (HK); Yin Ki Lau, Hong Kong (HK)

(73) Assignee: The Hong Kong Polytechnic University, Kowloon (HK)

( * ) Notice: Subject to any disclaimer, the term of this patent is extended or adjusted under 35 U.S.C. 154(b) by 650 days.

(21) Appl. No.: 11/122,325

(22) Filed: May 5, 2005

(65) Prior Publication Data
US 2006/0253008 A1 Nov. 9, 2006

(51) Int. Cl.
*A61B 5/1455* (2006.01)
(52) U.S. Cl. .................. 600/316; 600/322
(58) Field of Classification Search ......... 600/316, 600/319, 322
See application file for complete search history.

(56) References Cited

U.S. PATENT DOCUMENTS

| | | | |
|---|---|---|---|
| 4,286,327 A | 8/1981 | Rosenthal et al. | |
| 4,633,087 A | 12/1986 | Rosenthal et al. | |
| 5,077,476 A | 12/1991 | Rosenthal | |
| 5,086,229 A | 2/1992 | Rosenthal et al. | |
| 5,267,152 A | 11/1993 | Yang et al. | |
| 6,043,092 A | 3/2000 | Block | |
| 6,149,588 A * | 11/2000 | Noda et al. | 600/316 |
| 6,675,030 B2 * | 1/2004 | Ciurczak et al. | 600/316 |
| 6,741,876 B1 * | 5/2004 | Scecina et al. | 600/316 |
| 2004/0064299 A1 | 4/2004 | Mark et al. | |
| 2005/0065415 A1 * | 3/2005 | Cho et al. | 600/316 |
| 2005/0171415 A1 * | 8/2005 | Hirao | 600/316 |

* cited by examiner

*Primary Examiner*—Eric F. Winakur
*Assistant Examiner*—Etsub D Berhanu
(74) *Attorney, Agent, or Firm*—Leydig, Voit & Mayer, Ltd.

(57) ABSTRACT

A method for predicting blood glucose level of a person includes performing on the person a near-infrared spectral scan of a body part at a first group of wavelengths and at a second group of wavelengths, determining a first group of near-infrared absorbance values for the first group of wavelengths and a second group of near-infrared absorbance values for the second group of wavelengths, determining a first difference for the first group of near-infrared absorbance values and a second difference for the second group of near-infrared absorbance values, and calculating a blood glucose level for the person using the first and second differences.

14 Claims, 2 Drawing Sheets

METHOD FOR PREDICTING THE BLOOD GLUCOSE LEVEL OF A PERSON

BACKGROUND OF THE INVENTION

1. Field of the Invention

The current invention relates to methods for predicting a blood glucose level of a person using a near-infrared spectral scan of a body part of the person.

2. Description of Prior Art

People affected with diabetes must frequently monitor their blood glucose level. The traditional method of checking blood glucose level involves a finger prick to draw a drop of blood that is tested in an analytical device. It is often difficult, particularly for children and elderly people, to perform this test especially if it is needed several times a day.

There has been considerable research into non-invasive methods of predicting the blood glucose level of a person affected with diabetes. A popular method involves using a near-infrared (NIR) spectral scan of a body part of the person. When NIR light is radiated through the skin and into the blood vessels glucose molecules in the blood absorb some of the NIR light energy. The corresponding NIR absorbance can be used to predict the glucose level of the blood. The major problem with this method is accurately establishing an evaluation model for predicting the blood glucose level from the NIR spectral scan results. Various methods of establishing evaluation models are given in U.S. Pat. No. 6,675,030 to Ciurczak et al and its various references. The contents of U.S. Pat. No. 6,675,030 and the reference cited therein are incorporated in this application by reference to more fully describe the state of the art in this field.

A problem with most of the disclosed methods is that they are usually specific to the person being tested and the evaluation models are dynamic and often require recalibration.

SUMMARY OF THE INVENTION

It is an object of the present invention to provide a method for predicting a blood glucose level of a person using a near-infrared spectral scan that ameliorates the above mentioned problem or at least provides the public with a useful alternative.

According to a first aspect of the invention there is provided a method for predicting a blood glucose level of a person using a near-infrared spectral scan of a body part of the person, comprising performing on a person a near-infrared spectral scan of a body part at a first group of wavelengths and at a second group of wavelengths, determining a first group of near-infrared absorbance values for the first group of wavelengths and a second group of near-infrared absorbance values for the second group of wavelengths, determining a first second difference for the first group of near-infrared absorbance values and a second difference for the second group of near-infrared absorbance values, calculating a blood glucose level for the person using the first and second differences.

According to a second aspect of the invention there is provided a method for predicting a blood glucose level of a person using a near-infrared spectral scan of a body part of the person, comprising providing an evaluation model based on a population of test subjects, the evaluation model relating near-infrared absorbance of blood vessels of a body part of said test subjects at a first and second group of wavelengths to a glucose level of the blood vessels, performing on a person a near-infrared spectral scan of a body part at a first group of wavelengths and at a second group of wavelengths, determining a first group of near-infrared absorbance values for the first group of wavelengths and a second group of near-infrared absorbance values for the second group of wavelengths, and using the evaluation model to determine a blood glucose level for the person, the evaluation model comprising:

determining a first second difference for the first group of near-infrared absorbance values and a second difference for the second group of near-infrared absorbance values, dividing the first second difference with the second difference to find a first resultant, multiplying the first resultant by a first empirical constant to find a second resultant, and offsetting the second resultant by a second empirical constant.

Preferably, the first group of wavelengths comprises a first a second and a third wavelength within a range from 750 nm to 1700 nm and the second group of wavelengths comprises a fourth a fifth and a sixth wavelength within a range from 750 nm to 1700 nm.

Preferably, the first second and third wavelengths are within a range from 750 nm to 1125 nm and the fourth fifth and sixth wavelengths are within a range from 905 nm to 1701 nm.

Preferably, the first and second differences are determined using an equation of the form $d = A \cdot w1 + B \cdot w2 + C \cdot w3$ where d is the second difference; $w1$, $w2$ and $w3$ are the near-infrared absorbance values and A, B and C are constants Preferably, the spectral wavelength values are determined using a recursive method based on a population of test subjects.

Preferably, the blood glucose level is calculated using an equation of the form $c = D + (E \times (d1/d2))$ where c is the blood glucose level, $d1$ and $d2$ are the first and second differences and D and E are empirically determined constants.

Preferably, the constants D and E are determined using a linear regression based on a population of test subjects.

According to a third aspect of the invention there is provided a method of determining a blood glucose level of a person from near-infrared absorbance values obtained by a near-infrared spectral scan of a body part of the person, comprising dividing the absorbance values into first and second groups, determining a first second difference for the first group of absorbance values and a second difference for the second group of absorbance values, dividing the first second difference with the second difference to find a first resultant, multiplying the first resultant by a first empirical constant to find a second resultant, and offsetting the second resultant by a second empirical constant.

Further aspects of the invention will become apparent from the following drawings and description.

BRIEF DESCRIPTION OF THE DRAWINGS

Embodiments of the invention will now be described by way of example only and with reference to the accompanying drawings in which.

DESCRIPTION OF THE PREFERRED EMBODIMENTS

Figure 1:
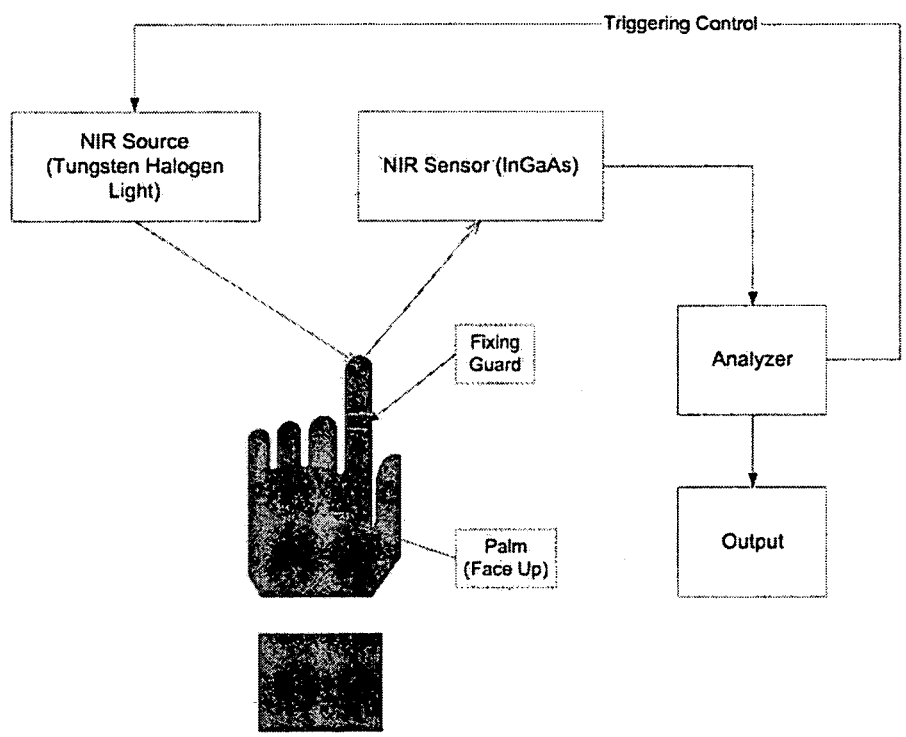
FIG. 1 is a schematic illustration of apparatus for obtaining a near-infrared spectral scan of a body part of a person.

In FIG. 1 there is depicted apparatus for performing a near-infrared (NIR) spectral scan of a body part of a person. The apparatus comprises a NIR light source and sensor for obtaining an NIR scan of a finger. The NIR scan signal from the sensor is processed by an analyser and a prediction of the person's blood glucose level output on a display.

Figure 2:
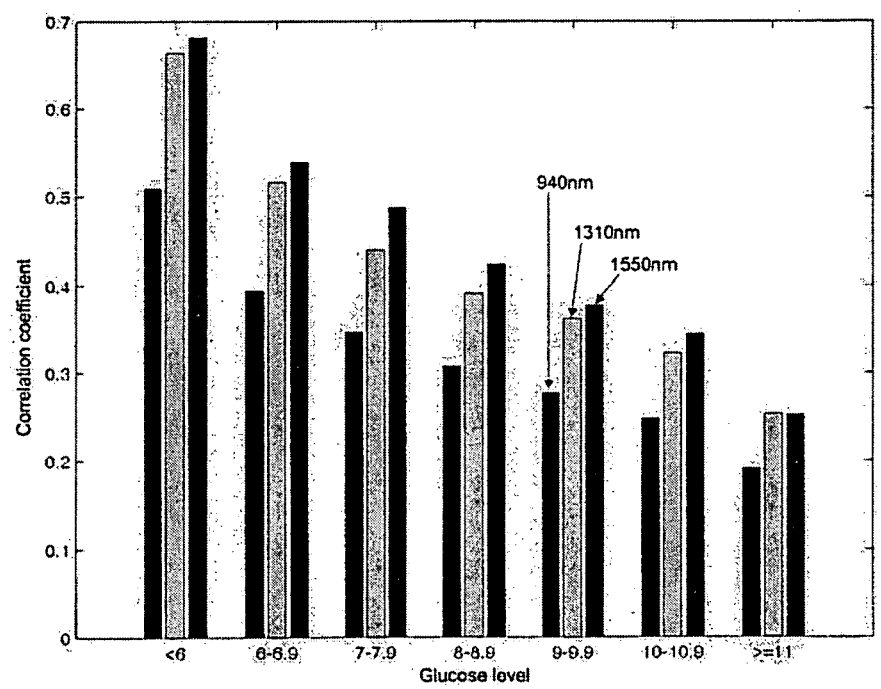
FIG. 2 illustrates correlation (or least square) coefficients of near-infrared absorbance of blood vessels of a body part at wavelengths of 940 nm, 1310 nm and 1550 nm to a glucose level of the blood vessels.

To predict the blood glucose level of the person using the NIR spectral scan an evaluation model was found based on a population of test subjects. The evaluation model relates NIR absorbance of blood vessels at a first and a second group of wavelengths to a glucose level of the blood vessels. The graph in FIG. 2 shows the relationship between the NIR absorbance of blood of a body part of the test subjects and the mean value of laboratory tested glucose levels of the test subjects at three sample wavelengths of 940 nm, 1310 nm and 1550 nm. The reference glucose levels are obtained using proven standard laboratory tests on blood samples from the test population. The linear relationship is found using a least squares method. The standard deviation on the mean value of the tested glucose levels for the test population was 10% to 20%.

The evaluation model is based on NIR absorbance scan of the blood vessels at six wavelengths $i-r1$, $i$, $i+r2$; $k-s1$, $k$ and $k+s2$: where $i$, $k$ are primary wavelengths and $r1$, $r2$, $s1$ and $s2$ are empirical values obtain from the test population. The NIR absorbance data is obtained from a NIR spectral scan using the apparatus of FIG. 1.

For the evaluation model the six wavelengths are divided into a first group (i) of three wavelengths comprising $i$, $i-r1$ and $i+r2$; and a second group (k) of three wavelengths comprising $k$, $k-s1$ and $k+s2$. In the preferred embodiment all six wavelengths are within the range 750 nm to 1700 nm. However, in other embodiments the first group of wavelengths $i$, $i-r1$ and $i+r2$ may be within a range from 750 nm to 1125 nm and the second group of wavelengths $k$, $k-s1$ and $k+s2$ may be within a range from 905 nm to 1701 nm.

First and second differences are determined for each group of wavelengths using the equation:

$$d = A \cdot w1 + B \cdot w2 + C \cdot w3$$

where d is the first or second difference; w1, w2, and w3 are NIR absorbance values at three particular wavelengths in the respective groups of wavelengths $i-r1$, $i$, and $i+r2$, and $k-s1$, $k$, and $k+s2$, and A, B and C are empirically determined constants. The preferred values of constants A, B, and C are 1, −2, and 1 respectively. Substituting for the six wavelengths the two equations become:

$$di = w(i-r1) - 2w(i) + w(i-r2) \text{ and}$$

$$dk = w(k-s1) - 2w(k) + w(k-s2)$$

The ratio of the first and second differences $di/dk$ is used to evaluate the glucose level of the person according to the equation:

$$C = D + (E \times (di/dk))$$

where, c is the predicted blood glucose level, and D and E are calibration coefficients for individual hardware obtained from a linear regression using the ratios of the first and second differences and the reference glucose levels obtained from the population of test subjects.

Figure 3:
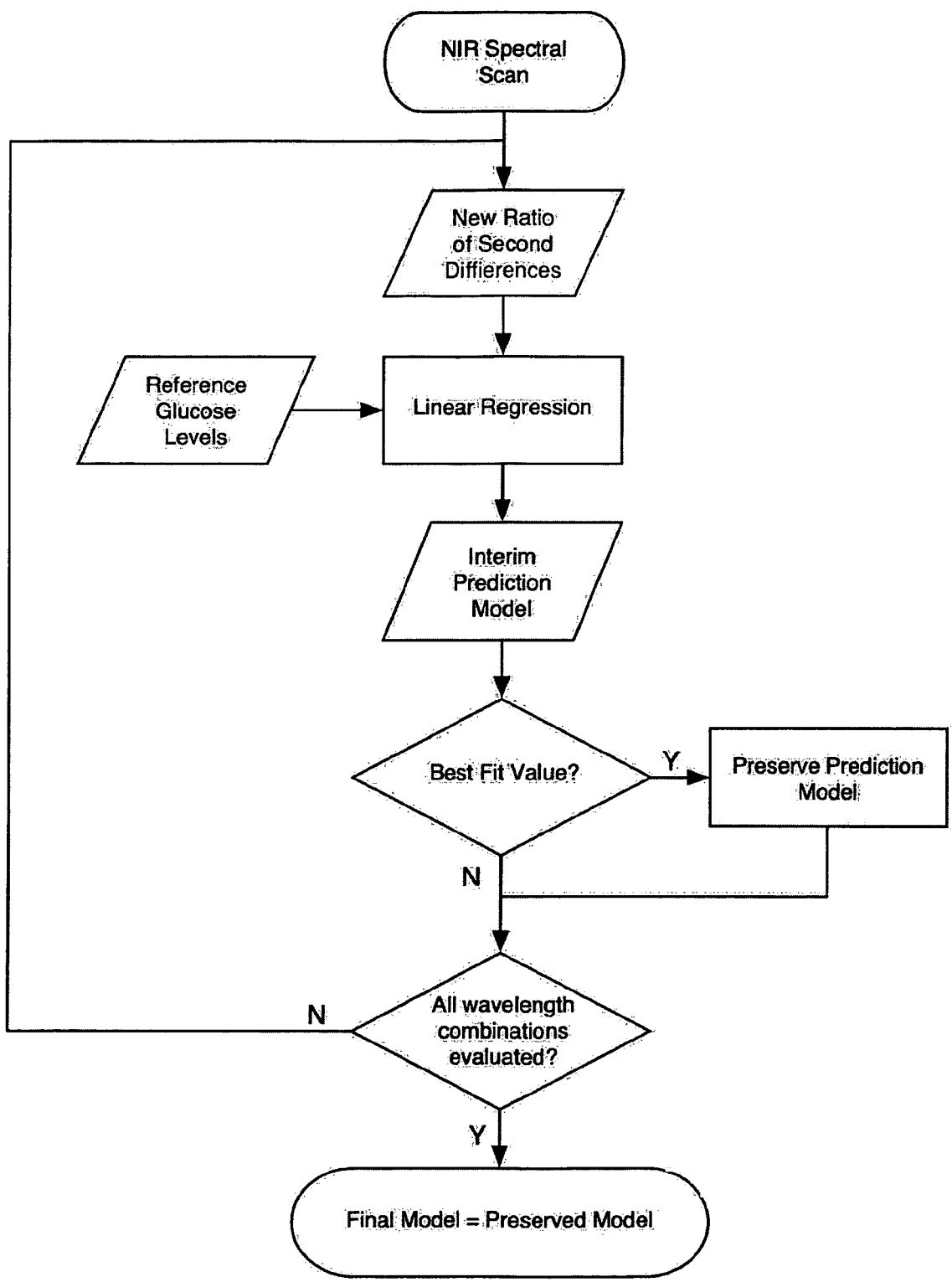
FIG. 3 is flow chart illustrating a recursive method used to determine optimum spectral wavelength values.

The optimum wavelengths in each group are determined using a recursive method. FIG. 3 illustrates a suitable recursive method used to evaluate every possible ratio of the differences obtained from every possible combination of wavelength parameters, i, k, r1, r2, s1, and s2, from the NIR spectral scan. During each recursion, the current ratio of the first and second differences is substituted into the evaluation equation. The best values for the constants D and E are determined by linear regression with cross-validation during each recursion.

The evaluated values for D and E along with the current ratio of the first and second differences produce an interim prediction model $Ci = D + (E \times (di/dk))$. The fitness of the interim prediction model is evaluated. If the interim prediction model in the current recursion generates a better fitness than all the previous prediction models, the previously preserved prediction model is discarded and replaced with the current interim prediction model. Otherwise, the current prediction model is discarded and the previously preserved prediction model is not altered. The recursion repeats until all possible combinations of wavelength parameters, thus all possible ratios of the first and second differences, are evaluated. When the recursion is finished the finally preserved prediction model which gives the best-fit result is selected as the final prediction model. The preferred ranges of constants D and E are between +/−30 and between +/−50, respectively.

The optimum wavelength varies for different fingers within the range of 750 nm to 1701 nm. Preferred values for r1, r2, s1, s2 and the wavelengths for each finger are given in the following table.

|               | r1 | r2 | I     | i − r1 | i + r2 | S1 | S2 | k     | k − s1 | k + s2 |
|---------------|----|----|-------|--------|--------|----|----|-------|--------|--------|
| Thumb         | 7  | 7  | 977   | 970    | 984    | 7  | 7  | 1,032 | 1,025  | 1,039  |
| Index finger  | 6  | 6  | 1,056 | 1,050  | 1062   | 6  | 6  | 1,511 | 1,505  | 1,517  |
| Middle finger | 15 | 15 | 939   | 924    | 954    | 15 | 15 | 1,139 | 1,124  | 1,154  |
| Ring finger   | 4  | 4  | 1,409 | 1,405  | 1413   | 4  | 4  | 1,024 | 1,028  | 1,028  |
| Last finger   | 6  | 6  | 1,031 | 1,025  | 1037   | 6  | 6  | 1,511 | 1,505  | 1,517  |

Where in the foregoing description reference has been made to integers or elements having known equivalents then such are included as if individually set forth herein.

Embodiments of the invention have been described, however it is understood that variations, improvement or modifications can take place without departure from the spirit of the invention or scope of the appended claims.

What is claimed is:

1. A method for predicting blood glucose level of a person using a near-infrared spectral scan of a body part of the person, comprising:

performing on a person a near-infrared spectral scan of a body part at a first group of wavelengths and at a second group of wavelengths, determining a first group of near-infrared absorbance values for the first group of wavelengths and a second group of near-infrared absorbance values for the second group of wavelengths, determining a first difference for the first group of near-infrared absorbance values and a second difference for the second group of near-infrared absorbance values, and calculating a blood glucose level for the person, using the first and second differences.

2. The method of claim 1 wherein the first group of wavelengths comprises first, second, and third wavelengths within a range from 750 nm to 1700 nm and the second group of wavelengths comprises fourth, fifth, and sixth wavelengths within a range from 750 nm to 1700 nm.

3. The method of claim 2 wherein the first, second, and third wavelengths are within a range from 750 nm to 1125 nm and the fourth, fifth, and sixth wavelengths are within a range from 905 nm to 1701 nm.

4. The method of claim 1 wherein the first and second differences are determined using an equation of the form:

$$d = A \cdot w1 + B \cdot w2 + C \cdot w3$$

where d is the first or second difference; w1, w2, and w3 are near-infrared absorbance values; and A, B, and C are constants.

5. The method of claim 2 wherein the first through sixth wavelengths are determined using a recursive method based on a population of test subjects.

6. The method of claim 1 wherein the blood glucose level is calculated using an equation of the form:

$$c = D + (E \times (d1/d2))$$

where c is the blood glucose level, d1 and d2 are the first and second differences, and D and E are empirically determined constants.

7. The method of claim 6 wherein the constants D and E are determined using a linear regression based on a population of test subjects.

8. A method for predicting blood glucose level of a person using a near-infrared spectral scan of a body part of the person, comprising:

providing an evaluation model based on a population of test subjects, the evaluation model relating near-infrared absorbance of blood vessels of a body part of the test subjects at first and second groups of wavelengths to a glucose level of the blood vessels, performing on a person a near-infrared spectral scan of a body part at a first group of wavelengths and at a second group of wavelengths, determining a first group of near-infrared absorbance values for the first group of wavelengths and a second group of near-infrared absorbance values for the second group of wavelengths, and using the evaluation model to determine a blood glucose level for the person, the evaluation model comprising:

determining a first difference for the first group of near-infrared absorbance values and a second difference for the second group of near-infrared absorbance values, dividing the first difference by the second difference to find a first resultant, multiplying the first resultant by a first empirical constant to find a second resultant, and offsetting the second resultant by a second empirical constant.

9. The method of claim 8 wherein the first group of wavelengths comprises first, second and third wavelengths within a range from 750 nm to 1700 nm and the second group of wavelengths comprises fourth, fifth and sixth wavelengths within a range from 750 nm to 1700 nm.

10. The method of claim 9 wherein the first, second, and third wavelengths are within a range from 750 nm to 1125 nm and the fourth, fifth, and sixth wavelengths are within a range from 905 nm to 1701 nm.

11. The method of claim 8 wherein the first and second differences are determined using an equation of the form:

$$d = A \cdot w1 + B \cdot w2 + C \cdot w3$$

where d is the first or second difference; w1, w2, and w3 are the near-infrared absorbance values; and A, B, and C are constants.

12. The method of claim 11 wherein the wavelengths are determined using a recursive method based on blood glucose levels of the population of test subjects.

13. The method of claim 8 wherein the first and second empirical constants are determined using a linear regression based on blood glucose levels of the population of test subjects.

14. A method of determining blood glucose level of a person from near-infrared (NIR) absorbance values obtained by a near-infrared spectral scan of a body part of the person, comprising:

dividing the NIR absorbance values into first and second groups, determining a first difference for the first group of absorbance values and a second difference for the second group of absorbance values, dividing the first difference by the second difference to find a first resultant, multiplying the first resultant by a first empirical constant to find a second resultant, and offsetting the second resultant by a second empirical constant.

* * * * *